United States Patent
Yamamoto et al.

(10) Patent No.: US 9,241,684 B2
(45) Date of Patent: Jan. 26, 2016

(54) ULTRASONIC DIAGNOSIS ARRANGEMENTS FOR COMPARING SAME TIME PHASE IMAGES OF A PERIODICALLY MOVING TARGET

(75) Inventors: Masa Yamamoto, Tokyo (JP); Naoko Ajiki, Tokyo (JP); Tetsuo Nakazawa, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 2079 days.

(21) Appl. No.: 11/721,445

(22) PCT Filed: Dec. 2, 2005

(86) PCT No.: PCT/JP2005/022177
§ 371 (c)(1),
(2), (4) Date: Oct. 14, 2009

(87) PCT Pub. No.: WO2006/064676
PCT Pub. Date: Jun. 22, 2006

(65) Prior Publication Data
US 2010/0036247 A1 Feb. 11, 2010

(30) Foreign Application Priority Data
Dec. 13, 2004 (JP) .................................. 2004-360221

(51) Int. Cl.
*A61B 8/14* (2006.01)
*A61B 6/03* (2006.01)
*A61B 8/00* (2006.01)
(Continued)

(52) U.S. Cl.
CPC . *A61B 8/14* (2013.01); *A61B 6/032* (2013.01); *A61B 6/566* (2013.01); *A61B 8/4254* (2013.01); *A61B 8/463* (2013.01); *A61B 8/483* (2013.01); *A61B 8/5238* (2013.01); *G01S 7/52088* (2013.01); *G01S 15/8993* (2013.01);
(Continued)

(58) Field of Classification Search
None
See application file for complete search history.

(56) References Cited

U.S. PATENT DOCUMENTS 5,159,931 A * 11/1992 Pini .............................. 600/443
6,488,629 B1 * 12/2002 Saetre et al. .................. 600/443
(Continued)

FOREIGN PATENT DOCUMENTS

JP    8-107895    4/1996
JP    10-151131   6/1998
(Continued)

OTHER PUBLICATIONS

English Translation of JP08-107895.*
(Continued)

*Primary Examiner* — Long V Le
*Assistant Examiner* — Bradley Impink
(74) *Attorney, Agent, or Firm* — Jones Robb, PLLC

(57) ABSTRACT

Previously captured three-dimensional image data of a subject from which a reference image is extracted are provided in the form of time-series volume data 14, 15 composed of two-dimensional image data groups which are recorded over at least one period of a periodically moving organ of the subject, with time-phase information of a biological signal of the subject added thereto. Two-dimensional image data whose time-phase information is identical with the time-phase information of the biological signal of the subject at the time when an ultrasonic image is captured are extracted from the three-dimensional image data so as to provide the reference image.

14 Claims, 10 Drawing Sheets

(51) Int. Cl.
*A61B 8/08* (2006.01)
*G01S 15/89* (2006.01)
*A61B 5/00* (2006.01)
*A61B 6/00* (2006.01)
*G01S 7/52* (2006.01)

(52) U.S. Cl.
CPC .............. *A61B5/7289* (2013.01); *A61B 6/5247* (2013.01); *A61B 8/56* (2013.01); *G01S 7/52074* (2013.01)

(56) References Cited

U.S. PATENT DOCUMENTS

| | | | |
|---|---|---|---|
| 7,006,593 B2* | 2/2006 | Kokubun et al. | 378/8 |
| 2002/0035329 A1 | 3/2002 | Kamiyama | |
| 2003/0161435 A1* | 8/2003 | Ozaki | 378/4 |
| 2004/0044283 A1 | 3/2004 | Yoneyama | |
| 2005/0119569 A1* | 6/2005 | Ohtake | 600/437 |
| 2005/0281444 A1* | 12/2005 | Lundberg et al. | 382/128 |
| 2007/0010743 A1* | 1/2007 | Arai | 600/443 |
| 2009/0054776 A1* | 2/2009 | Sasaki | 600/443 |

FOREIGN PATENT DOCUMENTS

| | | |
|---|---|---|
| JP | 2002-112998 | 4/2002 |
| JP | 2002-336255 | 11/2002 |
| JP | 2003-117010 | 4/2003 |
| WO | WO 03/045247 | 6/2003 |
| WO | WO 2004/098414 | 5/2004 |

OTHER PUBLICATIONS

English Translation of JP2002-336255.*
Takao Iwasaki et al.; Multiphase Realtime Virtual Sonography no Kaihatsu to Kongo no Kan Gazo Shindan ni Ataeru Eikyo; Acta Hepatological Japonica, Sep. 20, 2004; pp. 504-505; vol. 45, Suppl. 2.
Takao Iwasaki et al.; Real-Time Virtual Sonography (RVS); Sono Honshitsu Towa; Nov. 1, 2004; pp. 6-9; vol. 36; No. 12.

* cited by examiner

ULTRASONIC DIAGNOSIS ARRANGEMENTS FOR COMPARING SAME TIME PHASE IMAGES OF A PERIODICALLY MOVING TARGET

TECHNICAL FIELD

The present invention relates to an ultrasonic diagnosis apparatus, and particularly to a technique suitable for diagnosing an organ or the like which repeats a periodic motion, through comparison of a plurality of diagnostic images captured at different points in time.

BACKGROUND ART

An ultrasonic diagnosis apparatus enables real-time observation of an ultrasonic image of an arbitrary cross section of a subject. Therefore, such an ultrasonic diagnosis apparatus is effectively used to diagnose treatment effects or provide a guide for treatment, through comparison between a reference image captured, for example, before the treatment and an ultrasonic image captured after the treatment (or during the course of the treatment). A diagnostic image such as an ultrasonic image, an X-ray CT image, or an MR image can be used as the reference image. The reference image is generated by extracting, from three-dimensional image data (volume data) of the diagnostic image, two-dimensional image data at a slice position corresponding to the ultrasonic image.

Ultrasonic images are useful, because they are excellent in terms of real time feature, are suitable for observation of a moving organ, and can be captured by use of a simple apparatus. Meanwhile, diagnostic images captured by use of an X-ray CT apparatus or an MRI (magnetic resonance imaging) apparatus are excellent in terms of resolution, and therefore are suitable for use as a reference image. However, such diagnostic images have a characteristic of easily generating an artifact due to motion of an organ or the like.

For example, in the apparatus disclosed in Patent Documents 1 and 2, the position and posture of an ultrasonic probe operated in real time are detected so as to determine the slice position of an ultrasonic image, and a reference image of the same position as the ultrasonic image is extracted from volume data of X-ray CT images or MR images and is displayed on a screen of a monitor or the like.

Patent Document 1: Japanese Patent Application Laid-Open (kokai) No. Heisei 10-151131
Patent Document 2: Japanese Patent Application Laid-Open (kokai) No. 2002-112998

DISCLOSURE OF THE INVENTION

Problems to be Solved by the Invention

The conventional techniques described in Patent Documents 1 and 2 are effective for comparative diagnosis of a portion which hardly moves, such as the liver; however, the conventional techniques are not suitable for comparative diagnosis of a portion which moves periodically, such as the heart or peripheral blood vessel. That is, since X-ray CT images or MR images are likely to involve artifacts generated due to motion of an organ or the like, when volume data are created from a dynamic image, images are captured without being related to a biological signal representing the state of motion of the heart, peripheral blood vessel, or the like.

For example, when a pre-treatment image of, for example, an organ which moves periodically is compared with a post-treatment image of the organ, for proper analysis, the organ displayed in the pre-treatment reference image is desirably in the same motion state as that of the organ displayed in a real time image or reproduced image after the treatment (or in the course of the treatment). That is, in the case where a reference time phase is set for the period of the motion, and a plurality of time phases are set on the basis of the time delay from the referent time phase, the pre-treatment and post-treatment images to be compared desirably have the same time phase.

In this regard, according to the conventional techniques, an ultrasonic image and a reference image of different time phases must be compared for diagnosis, which may hinder comparative judgment used for, for example, diagnosing treatment effects or providing a guide for treatment.

An object of the present invention is to provide an ultrasonic diagnosis apparatus which can display, for accurate comparison, a plurality of diagnostic images of a periodically-moving organ or the like captured at different points in time.

Means for Solving the Problems

In order to achieve the above-described object, the present invention provides an ultrasonic diagnosis apparatus comprising ultrasonic-image creation means for reconstructing an ultrasonic image on the basis of a reflection echo signal measured by means of an ultrasonic probe which transmits ultrasonic waves to a subject and receives the ultrasonic waves from the subject; holding means for holding data of images of the subject captured in advance; reference-image creation means for extracting, from the captured-image data held in the holding means, a reference image corresponding to a sectional position of the ultrasonic image; and display means for displaying the ultrasonic image and the reference image, wherein the holding means holds the captured-image data with time phase information attached thereto; and the reference-image creation means extracts the reference image on the basis of the captured-image data corresponding to the time of capture of the ultrasonic image.

According to the present invention, the captured-image data with the information of a time phase corresponding to the time of capture of the ultrasonic image are extracted from the volume data, and a reference image is created. In this manner, the time phases of two captured images of a periodically moving organ are made coincident with each other or close to each other. Since an organ displayed in a reference image acquired before treatment and the organ displayed in a real time image or a reconstructed image obtained after the treatment (or during the treatment) can be compared with each other in the same motion state, the effects of the treatment or the like can be accurately diagnosed, and a guideline for the treatment can be provided.

Preferably, the time phase information is created on the basis of a biological signal of the subject, and the ultrasonic image is held in the holding means together with time phase information attached to the ultrasonic image.

In the case where the time phase information created on the basis of a biological signal of the subject is added to the ultrasonic image when it is held as described above, that ultrasonic image can be used as captured-image data from which the reference image is extracted at the time of subsequent diagnosis.

Notably, the time phase information showing the motion state of the organ of the subject can be obtained as follows. For example, when image analysis of the heart is performed, an electrocardiographic signal is used as a biological signal. With an R-wave of an electrocardiographic wave used as a reference time phase, the time delay from the R-wave can be set as the time-phase information.

Further, the apparatus of the present invention may be configured to hold the ultrasonic image together with the time-phase information and the type of a biological signal used to create the time-phase information, and to provide a warning (e.g., displaying a message) when the type of the biological signal added together with the time-phase information does not coincide with the type of a biological signal to be input.

Preferably, a plurality of captured-image data sets over at least one period of the periodically moving organ are held.

Preferably, captured-image data sets generated in accordance with a frame rate at which the ultrasonic image is displayed are held.

Preferably, a frame number reported in synchronism with the capture of the ultrasonic image and a time having elapsed from a reference time point (e.g., a time point at which the reference time phase is reported) to a time point at which the frame number is acquired are held in a related manner.

When the holding means does not hold the captured-image data at a time phase corresponding to the time point of capture of the ultrasonic image, preferably, the reference image is created through interpolation processing by use of captured-image data at different time phases.

As described above, the captured-image data corresponding to all possible time phases are not required to be held, and required captured-image data can be obtained through interpolation processing. Therefore, the hardware resources such as a storage device can be effectively used.

Preferably, the time phase information and a waveform of a biological signal of the subject or the like are displayed together with the ultrasonic image and the reference image.

When the time phase information is displayed together with the ultrasonic image and the reference image, the motion state of a diagnosed portion can be grasped on the display screen.

Preferably, a cut plane indicating a sectional position of the ultrasonic image is displayed together with the ultrasonic image and the reference image.

When a cut plane indicating a sectional position of the ultrasonic image is displayed together with the ultrasonic image and the reference image, the sectional position can be grasped on the display screen.

Preferably, the positional relation between the ultrasonic image and the reference image is set on the basis of the positional relation between a reference position designated on the captured-image data held in the holding means, and a reference position designated on the subject by means of the ultrasonic probe.

In this case, the positional relation between the ultrasonic image and the reference image can be set through a simple operation of designating respective reference positions on the captured-image data on the subject.

Preferably, the captured-image data held in the holding means are captured-image data which are obtained by means of an image diagnosis apparatus, such as an ultrasonic diagnosis apparatus, an X-ray CT apparatus, or an MR apparatus, and to which time phase information is added.

As described above, the captured-image data, which are data of images of the subject previously captured and held, can be obtained by use of another image diagnosis apparatus.

Preferably, the captured-image data obtained by means of an image diagnosis apparatus, such as an X-ray CT apparatus, are image data reconstructed on the basis of a biological signal of the subject.

When the image data reconstructed in synchronism with the electrocardiogram as described above are used, artifacts contained in the reference image can be reduced.

Notably, projection data used for reconstructing image data on the basis of a biological signal of the subject may be extracted while a predetermined time phase (e.g., a heart time phase of 80%; RR80%) is set as an end.

Effect of the Invention

According to the present invention, a plurality of diagnostic images obtained by imaging a periodically moving organ or the like at different times are displayed for accurate comparison.

DESCRIPTION OF REFERENCE NUMERALS

Figure 1:
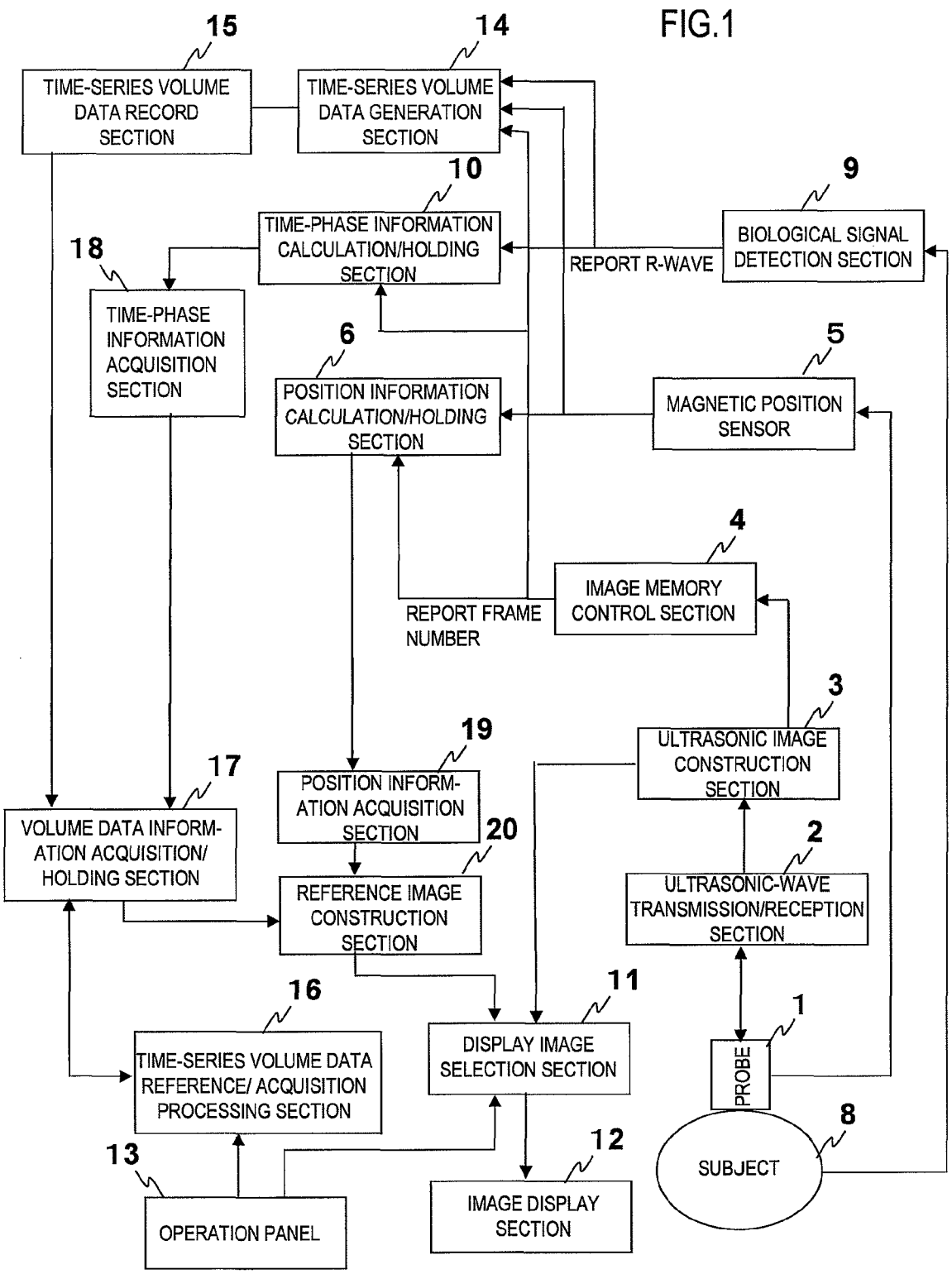
[FIG. 1] Block diagram of an ultrasonic diagnosis apparatus according to one embodiment of the present invention.

1 . . . probe
2 . . . ultrasonic-wave transmission/reception section
3 . . . ultrasonic image construction section
4 . . . image memory control section
5 . . . magnetic position sensor
6 . . . position information calculation/holding section
9 . . . biological signal detection section
10 . . . time-phase information calculation/holding section
11 . . . display image selection section
12 . . . image display section
13 . . . operation panel
14 . . . time-series volume data generation section
15 . . . time-series volume data record section
16 . . . time-series volume data reference/acquisition processing section
17 . . . volume data information acquisition/holding section
18 . . . time-phase information acquisition section
19 . . . position information acquisition section
20 . . . reference image construction section

BEST MODE FOR CARRYING OUT THE INVENTION

The present invention will next be described on the basis of embodiments.

(Embodiment 1)

FIG. 1 shows a block diagram of one embodiment of an ultrasonic diagnosis apparatus to which the present invention is applied. The ultrasonic diagnosis apparatus of the present embodiment realizes a function of sending and receiving ultrasonic waves to and from a subject, obtaining an ultrasonic image (B-mode image) of a portion to be diagnosed and displaying the image on a display screen, and extracting, from previously acquired volume data, a reference image of the same position and same time phase as the portion to be diagnosed and simultaneously displaying the reference image. In particular, the present embodiment is an example in which time-series volume data from which the reference image is extracted are generated from ultrasonic images.

As shown in FIG. 1, an ultrasonic probe 1 including a plurality of transducers is designed to convert an ultrasonic signal output from an ultrasonic-wave transmission/reception section 2 and transmit an ultrasonic wave to a subject 8, and to receive reflection echoes from various portions of the subject 8 and outputs a reflection echo signal to the ultrasonic-wave transmission/reception section 2. The ultrasonic-wave transmission/reception section 2 is designed to process the reflection echo signal output from the probe 1 and output the processed signal to an ultrasonic image construction section 3. This ultrasonic image construction section 3 reconstructs an ultrasonic image (B-mode image) of a portion to be diagnosed, on the basis of the input reflection echo signal, and stores the ultrasonic image in an image memory section of an image memory control section 4. This image memory control section 4 records and manages ultrasonic image data.

Figure 2:
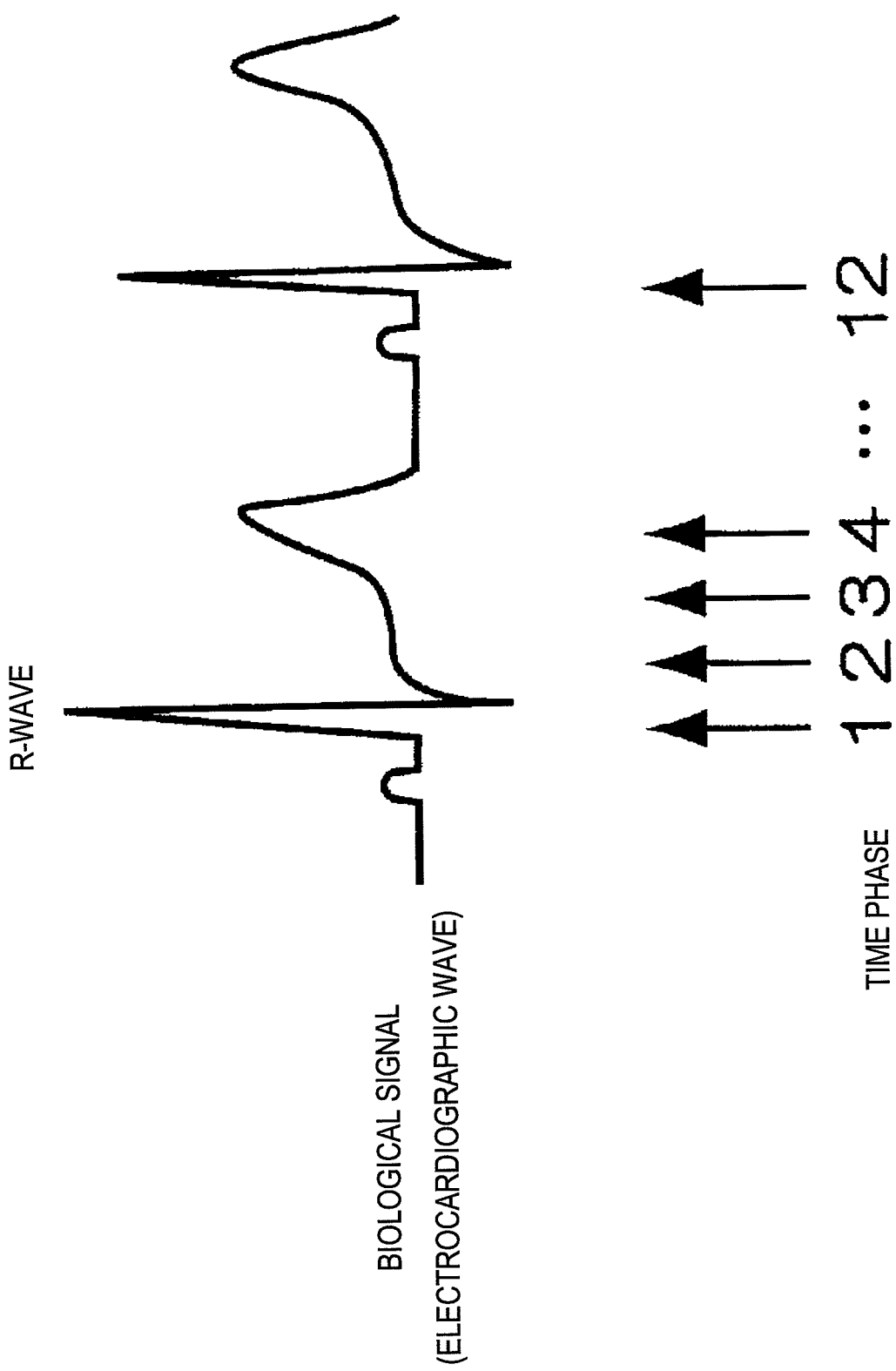
[FIG. 2] Diagram showing an electrocardiographic wave, which is an example biological signal.

A magnetic position sensor 5 detects the position and posture (angle) of the probe 1 on the basis of the three-dimensional coordinate system of the subject 8, and outputs the detected position and posture to a position information calculation/holding section 6. The position information calculation/holding section 6 obtains, through calculation, the slice plane position of an ultrasonic image to be captured, and holds the slice plane position, while relating it to the frame number of the ultrasonic image reported from the image memory control section 4. A biological signal detection section 9 receives a biological signal output from a biological signal measurement device attached to the subject 8, detects a predetermined reference time phase of the biological signal, and outputs the same to a time-phase information calculation/holding section 10. For example, on the basis of an electrocardiographic wave shown in FIG. 2, which is output from an electrocardiograph or the like, for example, an R-wave is detected and output as a reference time phase to the time-phase information calculation/holding section 10.

Meanwhile, the ultrasonic image once stored in the image memory control section 4 is transferred to an image display section 12 via a display image selection section 11, and is displayed on a screen in real time. Further, an operation panel 13 has a keyboard, a trackball, etc. By inputting commands from the operation panel 13, an operator can start respective sections relating to the display of the reference image, changeover the images displayed on the screen via the display image selection section 11, or change the display method.

Next, there will be described sections relating to generation of a reference image and generation of time-series volume data, which is a characteristic portion of the present embodiment. First, a time-series volume data generation section 14 is designed to generate time-series volume data, which are time-series three-dimensional image data, on the basis of the ultrasonic images stored in the image memory control section 4, detection data of the position and angle of the probe 1 detected by means of the magnetic position sensor 5, and the detection signal of the reference time phase output from the biological signal detection section 9. Further, two-dimensional-image frame numbers are added to the ultrasonic images transferred from the image memory control section 4 to the time-series volume data generation section 14, and the frame numbers are reported to the position information calculation/holding section 6 and the time-phase information calculation/holding section 10. As described above, the time-series volume data generation section 14 has a function of recording time-phase information simultaneously with the conventional processing of generating time-series volume data. The thus-generated time-series volume data are stored in a time-series volume data record section 15. Notably, the time-series volume data record section 15 is provided inside the ultrasonic diagnosis apparatus as in the present embodiment; however, it may be provided on a recording medium such as a CD, or a server or the like on a network.

Meanwhile, the biological signal detection section 9 detects the reference time phase of an electrocardiographic wave or a pulse wave; for example, in the case of the electrocardiographic wave, the detection section 9 detects an R-wave, and in the case of the pulse wave, the detection section 9 detects the position where the pulse wave assumes the maximum value, for example. A change in the signal of the electrocardiographic wave or the pulse wave input from the subject 8 is analyzed. For example, when the position of the R-wave of the electrocardiographic wave is to be detected, it is determined from a rising of the signal, height comparison, or the like. Upon detection of the reference time phase, which is a specific position of a biological signal, the biological signal detection section 9 immediately reports the reference time phase to the time-phase information calculation/holding section 10. The time-phase information calculation/holding section 10 starts counting of time from the time of the reported reference time phase. The time-phase information calculation/holding section 10 holds the counted time at the time when it acquires a frame number which is provided from the image memory control section 4 in synchronism with capture of an ultrasonic image, while relating it to the frame number. This counted time is reset when the next reference time phase is reported.

Figure 3:
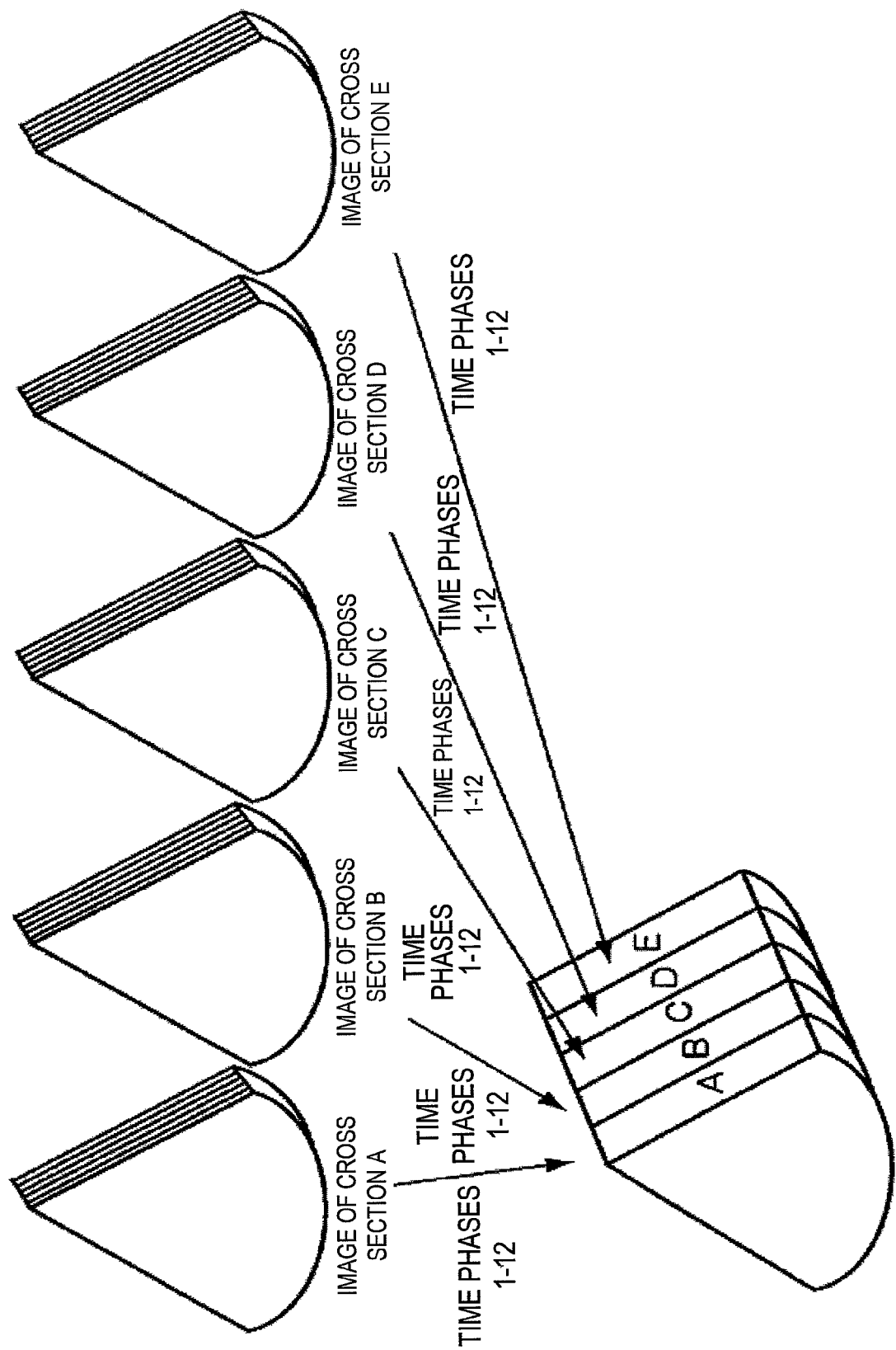
[FIG. 3] Diagram showing an example method for creating time-series volume data according to the present invention.

The time-series volume data generation section 14 can generate time-series volume data of ultrasonic images by use of a conventionally known method. That is, as shown in FIG. 3, a plurality of ultrasonic images of an arbitrary slice plane or cross section A are acquired over at least one period of the motion of an organ (e.g., one heart beat cycle), in synchronism with a plurality of time phases (e.g., time phases 1 to time phase 12 in FIG. 2) of equal time intervals, which are set with an arbitrary time phase (e.g., R-wave) used as a reference. The obtained ultrasonic images of the same slice plane are bundled together so as to create time-series volume data. This processing of creating time-series volume data of a single cross section is repeated for a plurality of cross sections (e.g., cross sections B to E), while the slice plane is shifted, whereby time-series volume data (A to E) of the plurality of cross sections are created. The time-series volume data of the plurality of cross sections created in this manner are sorted into time-series groups each including two-dimensional image data of the same time phase, whereby desired time-series volume data can be obtained.

Further, time phase information is added to each group including two-dimensional image data of the same time phase, and is recorded and held. Alternatively, the position of the two-dimensional image data group of the reference time phase may be held as information additional to the time-series volume data, for the following reason. Although the time phase of each volume data set may be held, when the position of the volume data of the reference time phase and the time interval of each slice plane are held, the position of three-dimensional image data (volume data) of the same time phase can be obtained through calculation.

The above-described method of generating time-series volume data is one example, and the time-series volume data may be generated by other methods, so long as the time-series volume data are recorded together with time-phase information added thereto. For example, even in the case of X-ray CT images or MR images, in the same manner as in the time-phase information calculation/holding section 10, time-phase information is generated on the basis of a biological signal, and two-dimensional images of each slice plane are recorded together with the time-phase information added thereto.

Although either of an electrocardiographic wave and a pulse wave may be used as a source of time-phase information, the source of the information must be recorded and held, for example, by adding an index to the time-phase information. This enables, when the reference-image display function of the present embodiment is started, checking of whether or not the type of a biological signal fed to the ultrasonic diagnosis apparatus coincides with the type of the biological signal of the time-series volume data. When they do not coincide with each other, a message to that effect is provided to a user.

Next, there will be described the processing steps for extracting, in response to a command from the operation panel 13, a reference image corresponding to an ultrasonic image displayed on the image display section 12, from the time-series volume data record section 15. First, a reference-image display command is fed from the operation panel 13 to a time-series volume data reference/acquisition processing section 16. Thus, a command is issued from the time-series volume data reference/acquisition processing section 16 to a volume data information acquisition/holding section 17. The volume data information acquisition/holding section 17 acquires the time-phase information of an ultrasonic image displayed on the image display section 12 from the time-phase information calculation/holding section 10 via a time-phase information acquisition section 18. The volume data information acquisition/holding section 17 then acquires, from the time-series volume data record section 15, volume data composed of a two-dimensional image data group with time-phase information which coincides with the time-phase information of the ultrasonic image displayed on the image display section 12, and holds the acquired volume data. Meanwhile, a position information acquisition section 19 acquires, from the position information calculation/holding section 6, the position information of the slice plane of the ultrasonic image displayed on the image display section 12.

A reference image construction section 20 extracts and reconstructs the reference image of the position corresponding to the slice plane of the ultrasonic image, from the volume data of the same time phase held in the volume data information acquisition/holding section 17. The reconstructed reference image is transferred to the image display section 12 via the display image selection section 11, and is displayed on the screen so that it can be compared with the ultrasonic image captured in real time.

In some cases, the time phase of the real-time ultrasonic image differs from the time phases of the time-series volume data sets previously acquired, due to a difference in the image-capturing method or the image-processing method. Accordingly, in many cases, the volume data information acquisition/holding section 17 fails to extract a volume data set whose time phase completely coincides with that of the real-time ultrasonic image. In such a case, a volume data set whose time phase is the closest to that of the real-time ultrasonic image may be selected. Further, when the time-series volume data are of X-ray CT images or MR images, in some cases the time phase intervals cannot be shortened. In such a case, a reference image can be obtained by, for example, performing interpolation on the basis of two two-dimensional image data sets within the time-series volume data, which set are close in time phase to the real-time ultrasonic image.

Alternatively, before generation of the time-series volume data, conditions for extracting ultrasonic images are determined, and the time-series volume data are generated in accordance with the frame rate at which the ultrasonic images are displayed, whereby the real-time ultrasonic image can be compared with a reference image whose time phase generally coincides with that of the real-time ultrasonic image.

The time-phase information acquisition section 18 operates as described above when it acquires and displays an ultrasonic image in real time. However, at the time of freeze; i.e., when a single ultrasonic image stored in the image memory control section 4 is displayed repeatedly, the time-phase information acquisition section 18 acquires the time-phase information of the ultrasonic image read from the image memory.

Further, in the present embodiment, the volume data information acquisition/holding section 17 holds a volume data set which is extracted from the time-series volume data record section 15 and whose time phase is the same as the ultrasonic image. However, the present invention is not limited thereto, and the volume data information acquisition/holding section 17 may be modified to hold information, such as the number of a volume data set of one time phase within the time-series volume data, which information becomes necessary when the volume data set is referred to. In such a case, the reference image construction section 20 extracts a reference image directly from the time-series volume data record section 15 in accordance with the number or like information.

Figure 4:
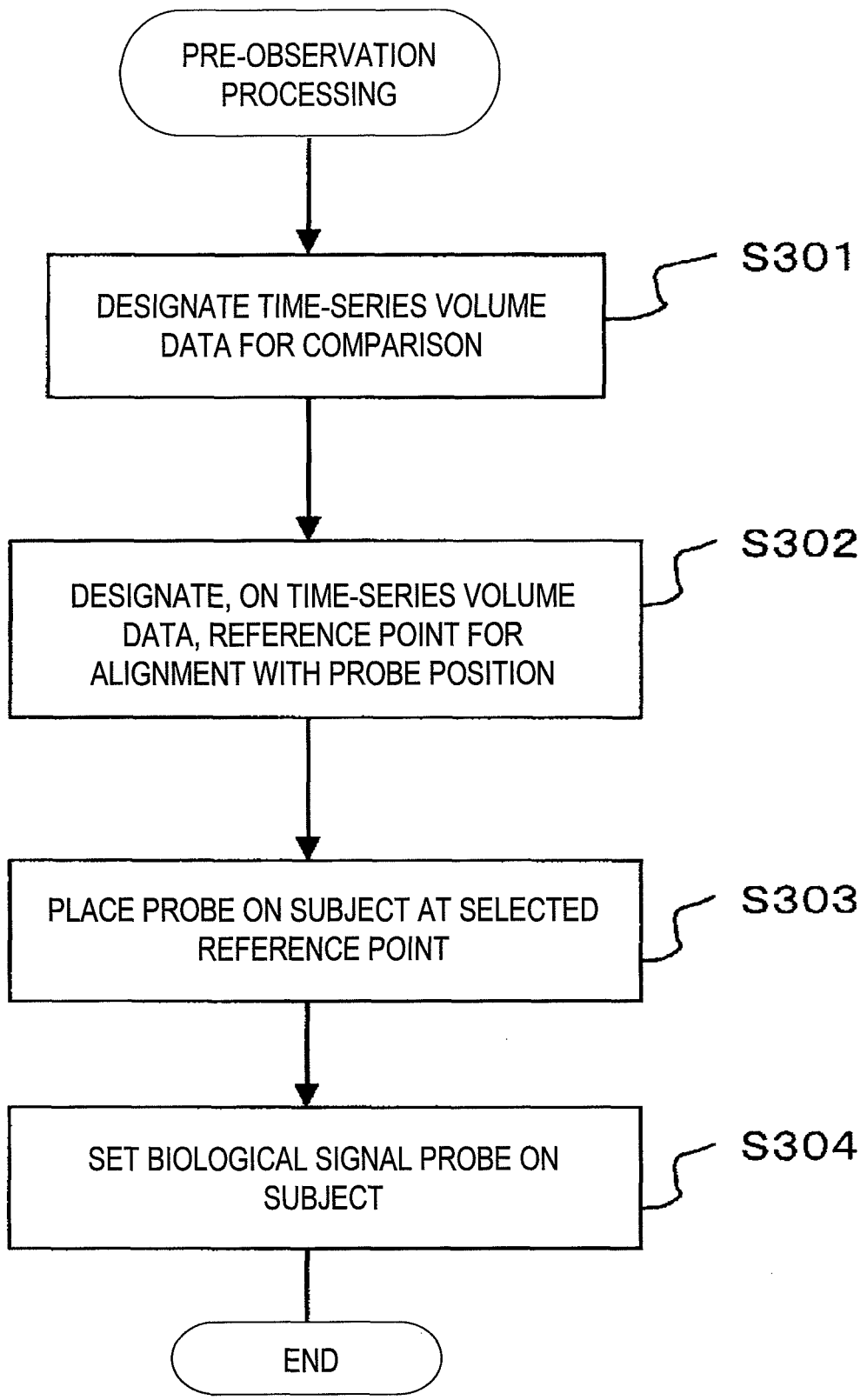
[FIG. 4] Flowchart showing the steps of processing performed before observation according to the embodiment of FIG. 1.

FIG. 4 shows the processing steps for acquiring time-series volume data, which must be acquired in advance before actual comparative observation is performed. First, an operator designates a time-series volume data set which is held in the time-series volume data record section 15 and is to be compared with a real-time ultrasonic image (S301). The designation is performed by designating a storage location or a name by use of a menu or the like. Next, the operator designates a position (X, Y, Z coordinates of the orthogonal coordinate system) on the designated time-series volume data set (S302), the position coinciding with the reference point position of the probe 1, which is designated in the next step. At this time, information regarding the probe 1 to be used may be input, and the reference value may be set in consideration of the maximum display width, etc., which change depends on the shape of the probe 1.

Next, the designated reference point position is set on the ultrasonic diagnosis apparatus side. That is, the operator brings the probe 1 into contact with the subject 8 at a position corresponding to the designated reference point, and inputs a setting execution command (S303) by use of the operation panel or the like. As a result, the positional relationship between an ultrasonic image and a reference image can be established. Further, a probe for acquiring a biological signal is set on the subject 8 (S304). For example, when an electrocardiogram is obtained, the probe is a set of electrodes. Operations up to this point are preparation for actual comparative observation.

Figure 5:
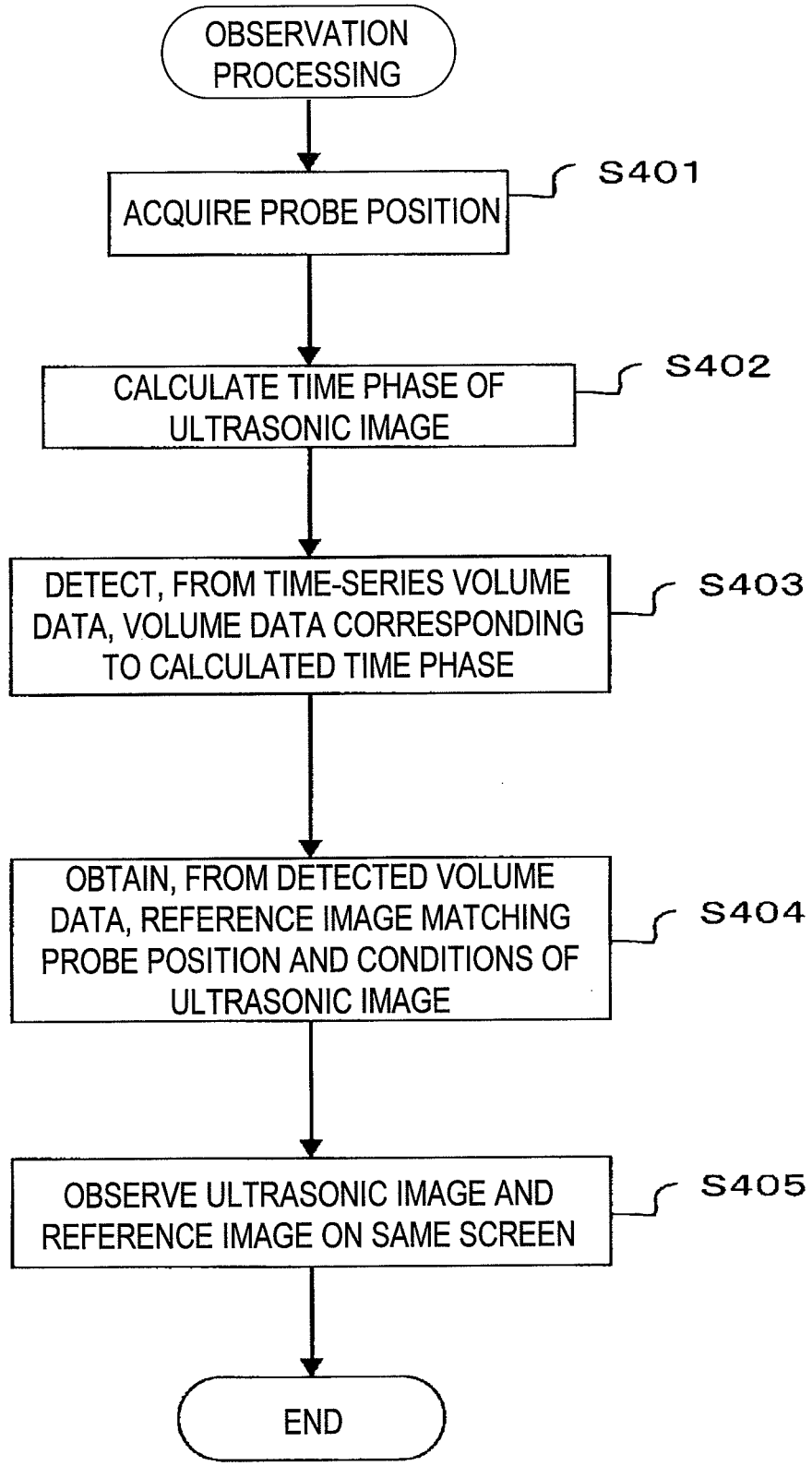
[FIG. 5] Flowchart showing the steps of processing performed during observation according to the embodiment of FIG. 1.

Next, the processing steps for performing actual comparative observation will be described with reference to FIG. 5.

While observing an image, the operator moves the probe 1, which has been set to the reference point by means of the pre-observation processing, to a region of interest. When the probe is moved, position information of the probe 1 is obtained from the magnetic position sensor 5, and position information of the probe 1 is calculated by the position information calculation/holding section 6, while being related to the captured ultrasonic image, and is recorded while being related to the frame number (S401). Next, on the basis of the detection information of the reference time phase obtained from the biological signal detection section 9, the time-phase information calculation/holding section 10 records the time phase information corresponding to each of the captured ultrasonic images, while relating the time phase information to the frame number (S402). Subsequently, in order to extract a reference image, a volume data set corresponding to the time phase of an ultrasonic image to be displayed is detected from the time-series volume data (S403). Next, a reference image is acquired from the detected volume data (S404), the reference image corresponding to the position of a slice plane of the ultrasonic image to be displayed, which slice plane is obtained by means of the position information calculation/holding section 6 on the basis of the position information of the probe 1. The thus-acquired reference image and the captured ultrasonic image are displayed on the screen of the image display section 12, whereby the ultrasonic image 21 and the reference image 22 of the same time phase and position can be observed in a comparative manner on the same screen as shown in FIG. 6 (S405).

Figure 6:
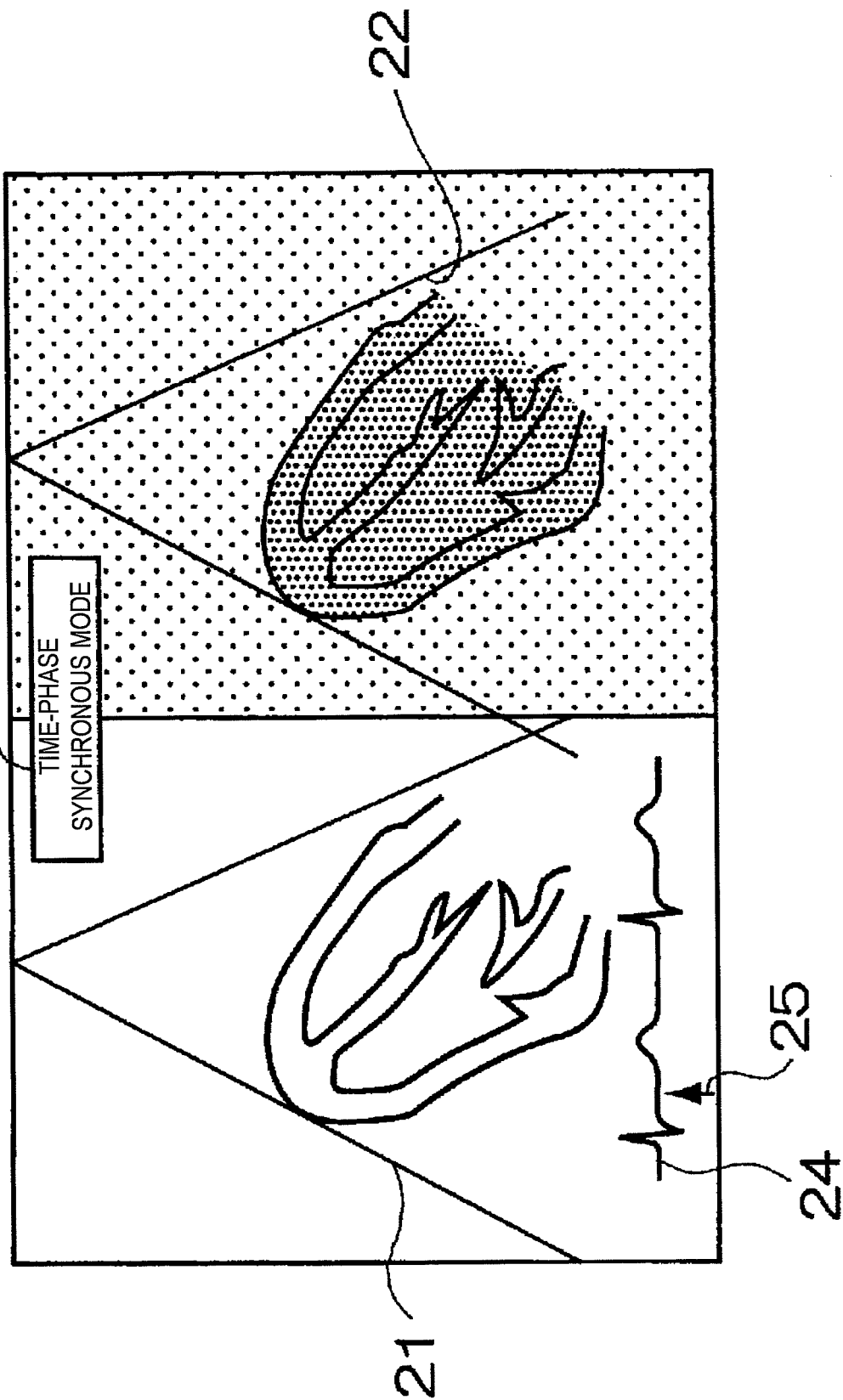
[FIG. 6] Diagram showing an example display screen according to the present invention.

In this case, as shown in FIG. 6, there may be added display of a "time-phase synchronous mode" 23 or the like phrase, which indicates that the images 21 and 22 are displayed while their time phases are synchronized. Further, the current time phase of the ultrasonic image 21 can be displayed by use of an arrow 25 superposed on an electrocardiographic wave 24. Further, the time phase of the reference image 22 may be displayed. Instead of the electrocardiographic wave 24 and the arrow 25, a bar chart or numerical values may be used to display the display time phase of a periodically moving organ.

Notably, in the case where the processing time for generating a reference image becomes longer than the time (FR) for generating an ultrasonic image, the time phases of the display images can be made coincident with each other by means of, for example, generating a preceding reference image or slightly delaying the display of the ultrasonic image on the screen, in consideration of the FR of the ultrasonic image and the reference image generation time. Further, the difference in time phase between the two images may be reported by displaying a diagram using wave forms, characters, or the like on the screen.

Further, when the reference image 22 is displayed, a three-dimensional image may be displayed on the same screen. In this case, the three-dimensional image may be displayed with its time-phase synchronized. This display of the three-dimensional image data can be realized by displaying the volume data acquired by the processing of step S403 of FIG. 5. Needless to say, the reference image described above can be displayed as a motion picture which moves with movement of the ultrasonic image.

(Embodiment 2)

Figure 7:
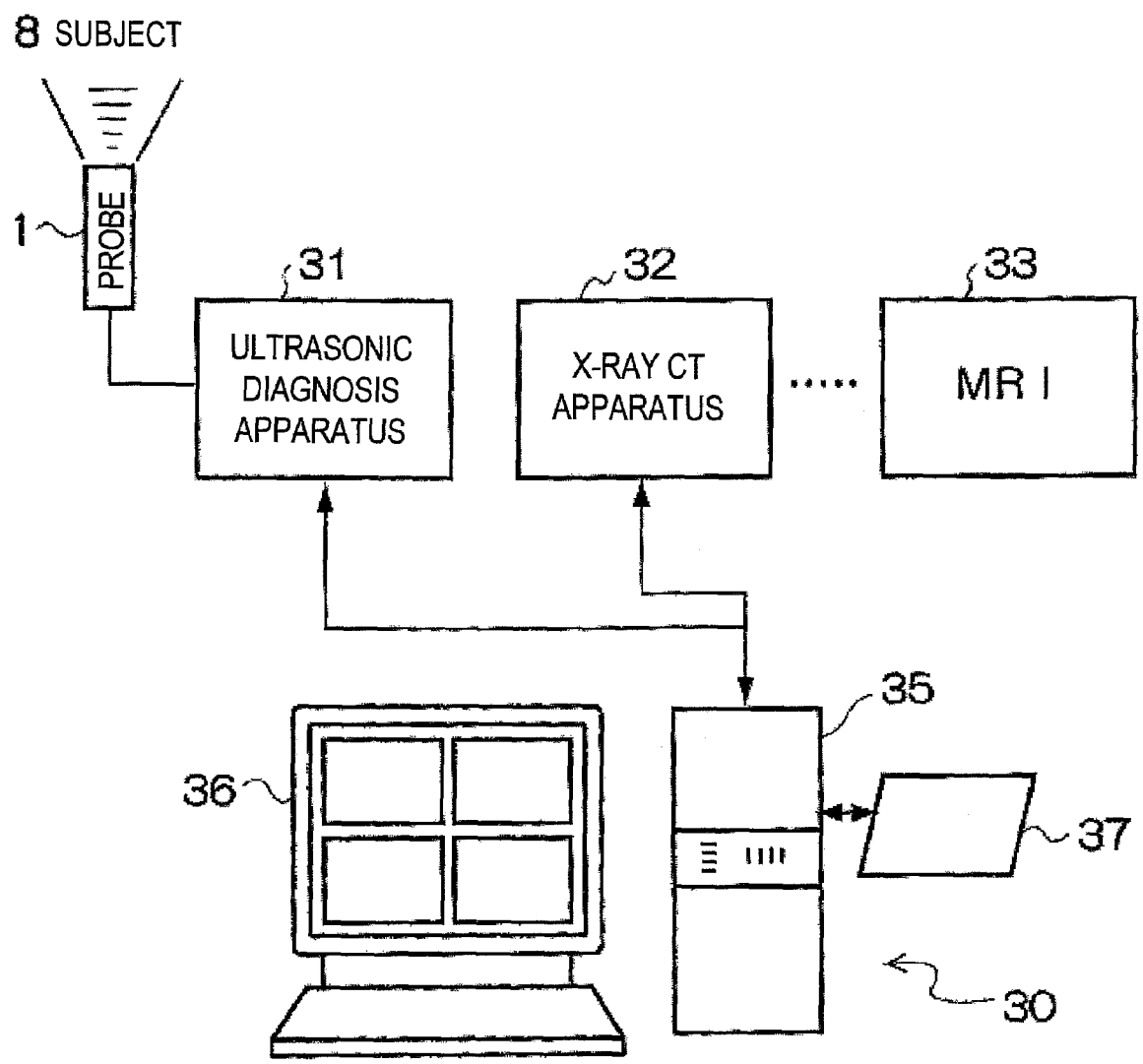
[FIG. 7] Block diagram showing an ultrasonic diagnosis apparatus according to another embodiment of the present invention.

FIG. 7 shows a block diagram of another embodiment of the ultrasonic diagnosis apparatus of the present invention. The present embodiment is configured such that an image processing/display apparatus 30, another ultrasonic diagnosis apparatus 31, an X-ray CT apparatus 32, and an image diagnosis apparatus 33 can be connected via, for example, a communication network. The image processing/display apparatus 30 has a function of generating a reference image on the basis of time-series volume data of three-dimensional images and displaying the reference image on a screen, and separately constitutes the characteristic portion of the embodiment of FIG. 1. In the present embodiment, time-series volume data captured by means of the X-ray CT apparatus 32 or the like are fed to a server 35 of the image processing/display apparatus 30, and if necessary, they are stored in a storage medium 37. An X-ray CT image whose time phase and cross section are identical with those of a real time image obtained by means of the ultrasonic diagnosis apparatus 31 is displayed on the monitor 36 of the image processing/display apparatus 30 as a reference image. Notably, needless to say, in place of the X-ray CT image, a diagnostic image captured by the image diagnosis apparatus 33 such as an MRI apparatus may be used as a reference image.

Figure 8:
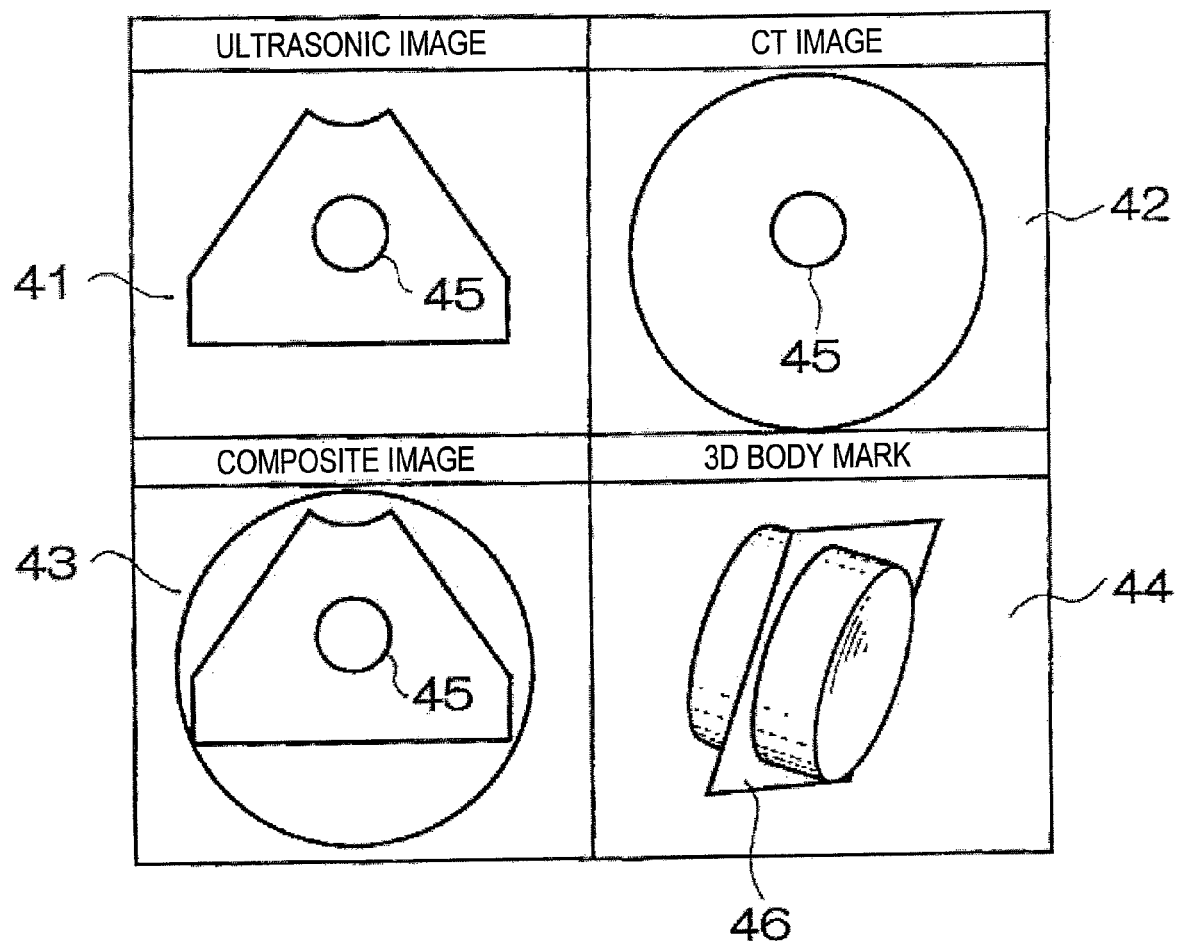
[FIG. 8] Diagram showing another example display screen according to the present invention.

According to the present embodiment, as shown in FIG. 8, an ultrasonic image 41 acquired in real time and a CT image 42 of the same cross section corresponding to the ultrasonic image 41 are displayed simultaneously. Further, a composite image 43 obtained by mixing the ultrasonic image 41 and the CT image 42 is displayed on the same screen. A common portion 45, which is a region of interest, is displayed on these images. Further, a three-dimensional CT image 44 is displayed on the same screen, and a cut plate 46, which shows the slice plane of the CT image 42, is displayed on the three-dimensional CT image 44.

In the present embodiment, time-series volume data such as those stored in the time-series volume data record section 15 of FIG. 1 are acquired by use of the X-ray CT apparatus 32, and stored in a recording medium or the like within the apparatus. That is, the time-series volume data acquired by use of the X-ray CT apparatus 32 are volume data which are acquired in time series over at least one period of a periodically moving organ or the like, in such a manner that coordinate information and time phase information based on a biological signal are added to data of a two-dimensional image including the same portion of the same subject as that to be diagnosed by the ultrasonic diagnosis apparatus 31.

The image processing/display apparatus 30 of the present embodiment receives the time-series volume data from the X-ray CT apparatus 32 via a connection medium such as a network, and stores them into the server 35; creates, through calculation by the server 35, a reference image whose time phase and position are identical with those of the real time image input from the ultrasonic diagnosis apparatus 31; and displays the reference image on a monitor 36, for example, in a manner as shown in FIG. 8.

For example, in the case of an organ whose motion is small, such as the liver, image capturing is performed at the same location without moving the probe of the ultrasonic diagnosis apparatus 31, and the ultrasonic image 41 of FIG. 8 does not move. Therefore, the CT image 42 does not change. However, in the case where the image capturing portion is not the liver but the heart, since the heart beats, the ultrasonic image 41 obtained by the ultrasonic diagnosis apparatus 31 capable of displaying a real-time image is displayed to change with time. Naturally, the ultrasonic image changes even when the position of the probe is not moved. In order to cope with such changes, according to the present embodiment, the CT image 42 is displayed to change with time.

Incidentally, in the case where an image of the heart is captured by use of the X-ray CT apparatus 32, if an ordinary image reconstruction method is used, a motion artifact due to motion of the heart is generated, and a clinically effective image cannot be obtained. An ECG synchronized reconstruction technique is a known method for reducing such a motion artifact due to motion. According to this technique, when CT photographing is performed, electrodes of a cardiograph are attached to a patient; cardiogram information is obtained during the CT photographing; and images at the end of the contraction period or the expansion period of the heart during which the motion of the heart is relatively small are created on the basis of the cardiogram information.

Figure 9:
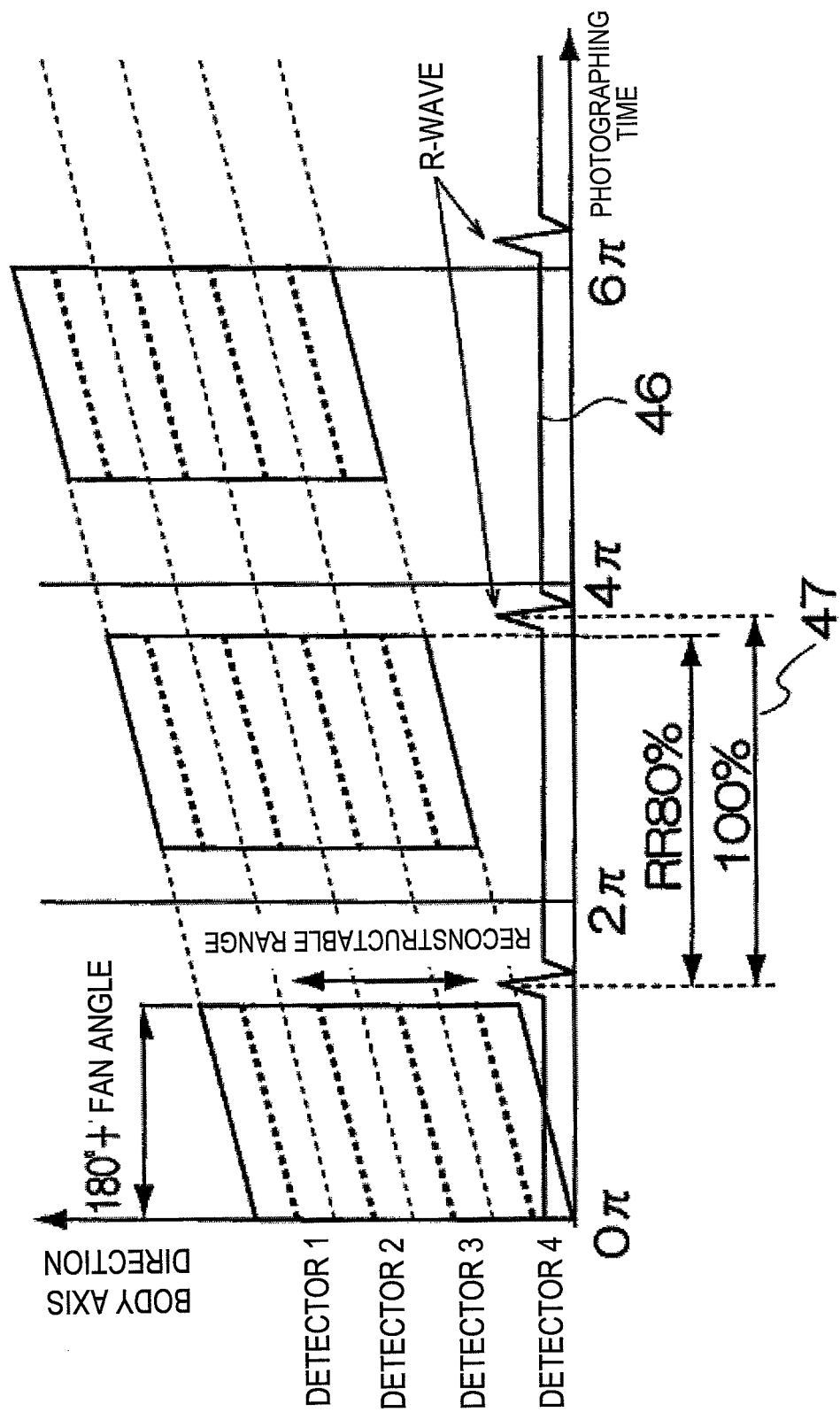
[FIG. 9] Explanatory view showing an example ECG reconstruction method.
Figure 10:
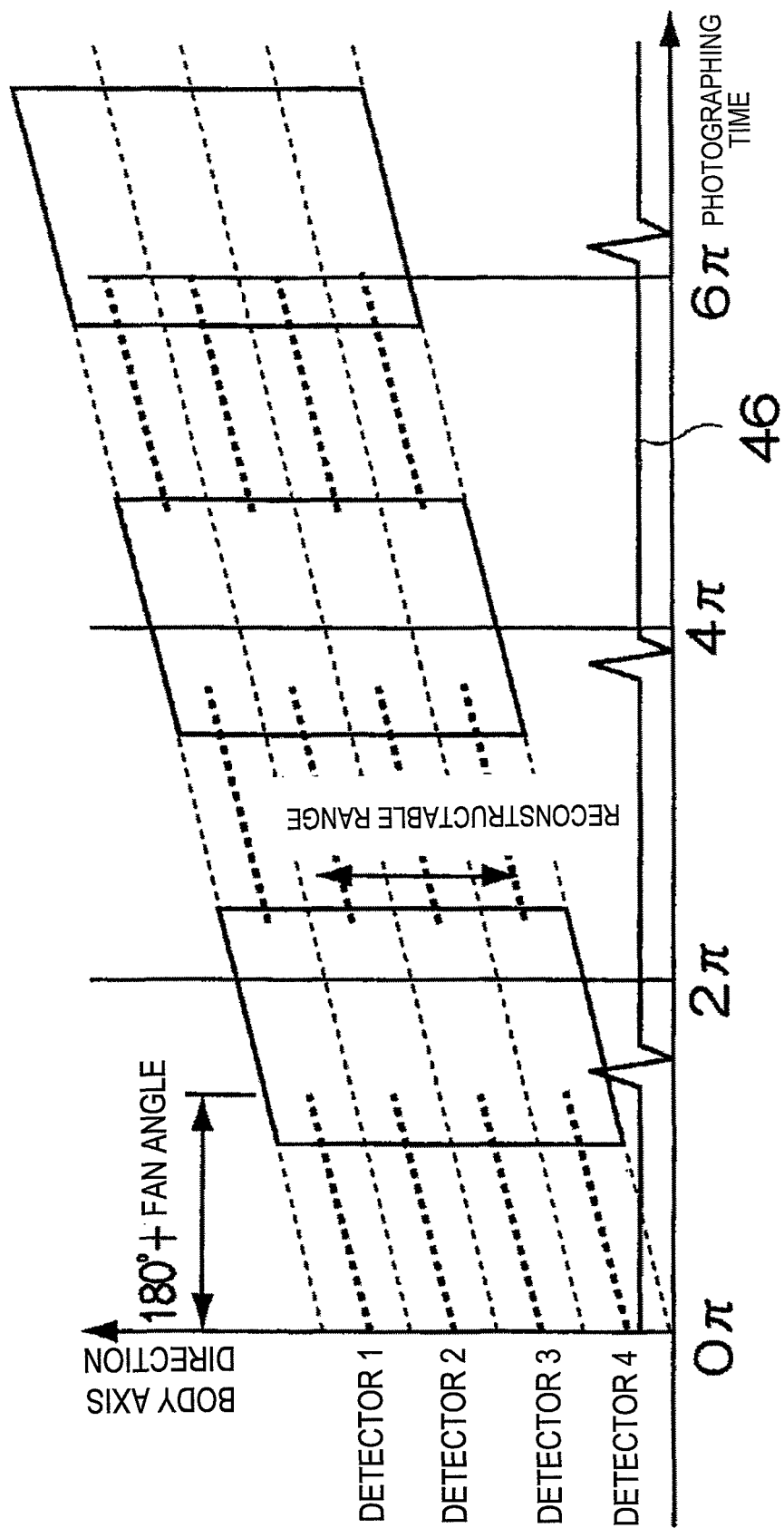
[FIG. 10] Explanatory view showing another example ECG reconstruction method.

This ECG reconstruction method will be described with reference to FIG. 9. In the present embodiment, a reconstruction method, generally called "ECG half reconstruction," is employed. However, the present invention is not limited to the ECG half reconstruction method. In FIG. 9, the horizontal axis represents the photographing time by photographing angle, and the vertical axis represents the body axis direction. FIG. 9 shows loci of detectors (1 to 4) of a 4-line multi-slice CT when it performs spiral scanning, and showing an electrocardiographic wave 46 superposed thereon. Only the R-wave of the electrocardiographic wave 46 is displayed, for preventing the display from becoming complex. Further, in the example of ECG reconstruction of FIG. 9, projection data are extracted so that, with the interval 47 between adjacent R-waves represented by 100%, the end of projection data required for ECG reconstruction is located at the 80% position. This position corresponds to the expansion period of the heart; in the case of an X-ray CT apparatus equipped with a scanner which requires 0.5 seconds for one revolution so as to use the half reconstruction method, an image of the heart expansion period of about 300 ms can be obtained. The above-described 80% location is generally represented by heart time phase 80%, RR80%, or the like. FIG. 10 shows an example in which the heart time phase has been shifted. FIG. 10 shows an ECG half reconstruction possible range at the RR40% position, which is the end of the heart contraction. The technique of performing ECG reconstruction, while shifting the RR time phase as described above, to thereby obtain a motion-artifact-reduced tomogram image of the hear at an arbitrary time phase is the above-mentioned ECG synchronized reconstruction method.

The X-ray CT apparatus 32 of FIG. 7 also can create the ECG reconstructed image of each time phase. Further, the image processing/display apparatus 30 can create the ECG reconstructed image. The image processing/display apparatus 30 has the following feature. As shown in FIG. 7, the slice position information and the time-phase information of an ultrasonic image of the heart obtained by means of the ultrasonic diagnosis apparatus 31 are supplied to the image processing/display apparatus 30. The image processing/display apparatus 30 reads, from a storage medium such as a HDD of the X-ray CT apparatus 32, time-series volume data whose time phase is generally identical with that of the ultrasonic image, and transfers the volume data to the storage medium 37 of the image processing/display apparatus 30. Subsequently, the image processing/display apparatus 30 extracts a reference image corresponding to the ultrasonic image from the time-series volume data held in the storage medium 37 and being of the time phase generally identical with that of the ultrasonic image, and displays the reference image on the monitor 36. The above-described ECG reconstruction method is a two-dimensional reconstruction method. In the present embodiment, a three-dimensional reconstruction method can be applied while a cone-beam reconstruction method is used as an ECG reconstruction method. This cone-beam reconstruction method is a known method of creating a three-dimensional image directly from measurement data without creating two-dimensional images.

The image processing/display apparatus 30 can obtain a real-time ultrasonic image of the beating heart captured by the ultrasonic diagnosis apparatus 31, and smoothly display the motion of the CT-image reference image corresponding to the ultrasonic image. In this case, the time-series volume data transferred from the X-ray CT apparatus 32 must be fine data for each R-R time phase period. For example, in the case where an ECG reconstructed image is calculated and stored for each 1% section of the R-R time phase period, a storage area of 10 GB is required in total if 200 images are captured along the body axis direction. Such a storage area can be realized through an improvement of the hardware configuration; however, this is not practical. Therefore, the image processing/display apparatus 30 of the present embodiment creates the time-series volume data as follows.

That is, for example, ECG reconstructed images of 10 time phases (corresponding to the 0% to 90% positions (10% intervals)) of the R-R time phase period are created by the X-ray CT apparatus 32 or the image processing/display apparatus 30, and the time-series volume data are created on the basis of the ECG reconstructed images. When the heart time phase of the ultrasonic image obtained at the ultrasonic diagnosis apparatus 31 is 45%, the image processing/display apparatus 30 creates an image at the heart time phase of 45% through image interpolation, from data for the heart time phases of 50% and 40% of the previously created above-mentioned time-series volume data.

The interpolation used here may be a simple linear interpolation or a higher-order interpolation. This method enables the ECG-corrected ultrasonic image of the heart at an arbitrary timing to be displayed to match the actual ultrasonic diagnosis apparatus 31. Notably, when 10 time phases are insufficient for visual observation, finer time-series volume data of, for example, 20 time phases can be created in advance.

According to the present embodiment, even in the case of ultrasonic images of a periodically moving organ such as the heart, it becomes possible to perform image diagnosis while comparing the real-time ultrasonic image obtained at the ultrasonic diagnosis apparatus 31 and the CT-image reference image, whereby the image diagnosis performance can be improved remarkably.

Notably, in the present embodiment, the heart is taken as an example of periodically moving organs. The present invention is similarly applied to the image diagnosis of the lung which moves with breathing. In this case, time phases are set on the basis of a biological signal obtained by measuring the breathing movement by use of a breathing monitor.

Preferred embodiments of the ultrasonic diagnosis apparatus according to the present invention have been described with reference to the accompanying drawings. However, the present invention is not limited to the above-described embodiments. It is clear that a person with ordinary skill in the art can easily conceive various modifications and changes within the technical idea disclosed herein, and it is contemplated that such modifications and changes naturally fall within the technical scope of the present invention.

The invention claimed is:

1. An ultrasonic diagnosis apparatus comprising: an ultrasonic probe configured to transmit ultrasonic waves to a subject and receive ultrasonic waves from the subject;
    a computer including at least one processor, performing operations including:
        reconstructing an ultrasonic image captured in real time, on a basis of a reflection echo signal measured by the ultrasonic probe;
        holding volume data of the subject captured in advance, in a non-transitory storage medium;

extracting, from the volume data held in the storage medium, a reference image corresponding to a sectional position of the ultrasonic image captured in real time; and displaying a reconstructed said ultrasonic image captured in real time and the reference image, wherein:

the holding holds time-series volume data of plural shifted slice-planes of the subject captured in advance, in which time phase information are attributed to two-dimensional image data of respective time-series cross-sectional images taken in each slice-plane, and the two-dimensional image data of the cross-sectional images of the slice planes, are sorted via the time phase information into two-dimensional image data groups, with each respective two-dimensional image data group including the two-dimensional image data having time-phase information of a same time phase; and the extracting acquires, from the storage medium, volume data composed of a two-dimensional image data group with time-phase information which coincides with the time-phase information of the ultrasonic image captured in real time, and extracts and reconstructs the reference image from volume data which has a slice plane which coincides to a slice plane of the ultrasonic image captured in real time;

the time-phase information and a type of a biological signal indicated as an input to the ultrasonic diagnosis apparatus and used to create the time-phase information, are added to the two-dimensional image data of respective cross sections of volume data held in the storage medium; and when a reference-image display function is started, the ultrasonic diagnosis apparatus checks whether or not the type of a biological signal fed to an input of the ultrasonic diagnosis apparatus in connection with real-time said reflection echo signal measured by an ultrasonic probe, coincides with the type of the biological signal added to the two-dimensional image data of respective cross-sections of the volume data held in the storage medium, and provides a warning when coincidence is not found.

2. An ultrasonic diagnosis apparatus according to claim 1, wherein:

the computer including at least one processor, performing further operations including:

creating the time phase information on a basis of a biological signal of the subject; and adding the time phase information created by the creating to a reconstructed said ultrasonic image captured in real time, wherein the volume data held in the storage medium are created by the reconstructing and are ultrasonic images to which the time-phase information is added by the time-phase information adding component.

3. An ultrasonic diagnosis apparatus according to claim 1, wherein the volume data held in the storage medium include a plurality of the two-dimensional image data over at least one periodic period of a periodically moving organ of the subject.

4. An ultrasonic diagnosis apparatus according to claim 1, wherein time-series volume data sets generated in accordance with a frame rate at which the ultrasonic image captured in real time is displayed, are held in the storage medium.

5. An ultrasonic diagnosis apparatus according to claim 1, wherein a frame number reported in synchronism with capture of the ultrasonic image captured in real time, is added to the two-dimensional image data of respective cross sections of the volume data held in the storage medium; and the storage medium holds a counted time occurring when the frame number is reported in synchronism with capture of the ultrasonic image captured in real time, while relating the counted time to the frame number.

6. An ultrasonic diagnosis apparatus according to claim 1, wherein when the storage medium does not hold the two-dimensional image data having time phase information which coincides with the time-phase information of the ultrasonic image captured in real time, the extracting creates the reference image through interpolation processing by use of two-dimensional image data at different time phases.

7. An ultrasonic diagnosis apparatus according to claim 1, wherein the displaying displays the time phase information together with the ultrasonic image captured in real time and the reference image.

8. An ultrasonic diagnosis apparatus according to claim 1, wherein the displaying displays a cut plane indicating a sectional position of a reconstructed said ultrasonic image captured in real time, together with the reconstructed said ultrasonic image captured in real time and the reference image.

9. An ultrasonic diagnosis apparatus according to claim 1, wherein:

the computer including at least one processor, performing a further operation including:

setting a positional relation between the ultrasonic image captured in real time and the reference image on a basis of the positional relation between a reference position designated on the volume data held in the storage medium, and a reference position designated on the subject by the ultrasonic probe.

10. An ultrasonic diagnosis apparatus according to claim 1, wherein the volume data held in the storage medium are captured by an image diagnosis apparatus, and the time phase information created on a basis of a biological signal, is added to the volume data.

11. An ultrasonic diagnosis apparatus according to claim 1, wherein the volume data held in the storage medium are image data synchronized with a biological signal of the subject.

12. An ultrasonic diagnosis apparatus comprising: an ultrasonic probe configured to transmit ultrasonic waves to a subject and receive ultrasonic waves from the subject;

a computer including at least one processor, performing operations including:

reconstructing an ultrasonic image captured in real time, on a basis of a reflection echo signal measured by the ultrasonic probe;

holding volume data of the subject captured in advance, in a non-transitory storage medium;

extracting, from the volume data held in the storage medium, a reference image corresponding to a sectional position of the ultrasonic image captured in real time; and displaying a reconstructed said ultrasonic image captured in real time and the reference image, wherein:

the holding holds time-series volume data of plural shifted slice-planes of the subject captured in advance, in which time phase information are attributed to two-dimensional image data of respective time-series cross-sectional images taken in each slice-plane; and the extracting acquires, from the storage medium, the two-dimensional image data of a time-series cross-sectional image having a slice plane which coincides with a slice plane of the ultrasonic image captured in real time and having time-phase information which coincides with the time-phase information of the ultrasonic image captured in real time, and reconstructs the reference image of the position corresponding to a slice plane of the ultrasonic image captured in real time, from the acquired two-dimensional image data; and when a reference-image display function is started, the ultrasonic diagnosis apparatus checks whether or not the type of a biological signal fed to an input of the ultrasonic diagnosis apparatus in connection with real-time said reflection echo signal measured by an ultrasonic probe, coincides with the type of the biological signal added to the two-dimensional image data of respective cross-sections of the volume data held in the storage medium, and provides a warning when coincidence is not found.

13. An ultrasonic diagnosis method comprising:

reconstructing an ultrasonic image captured in real time, on a basis of a reflection echo signal measured by an ultrasonic probe which transmits ultrasonic waves to a subject and receives the ultrasonic waves from the subject;

holding volume data of the subject captured in advance;

extracting, from the volume data, a reference image corresponding to a sectional position of the ultrasonic image captured in real time; and displaying a reconstructed said ultrasonic image captured in real time and the reference image, wherein:

the holding holds time-series volume data of plural shifted slice-planes of the subject captured in advance, in which time phase information are attributed to two-dimensional image data of respective time-series cross-sectional images taken in each slice-plane, and the two-dimensional image data of the cross-sectional images of the slice planes, are sorted via the time phase information into two-dimensional image data groups, with each respective two-dimensional image data group including the two-dimensional image data having time-phase information of a same time phase; and the extracting acquires, volume data composed of a two-dimensional image data group with time-phase information which coincides with the time-phase information of the ultrasonic image captured in real time, and extracts and reconstructs the reference image from volume data which has a slice plane which coincides to a slice plane of the ultrasonic image captured in real time;

the time-phase information and a type of a biological signal indicated as an input to the ultrasonic diagnosis apparatus and used to create the time-phase information, are added to the two-dimensional image data of respective cross sections of volume data; and when a reference-image display function is started, the ultrasonic diagnosis apparatus checks whether or not the type of a biological signal fed to an input of the ultrasonic diagnosis apparatus in connection with real-time said reflection echo signal measured by an ultrasonic probe, coincides with the type of the biological signal added to the two-dimensional image data of respective cross-sections of the volume data, and provides a warning when coincidence is not found.

14. An ultrasonic diagnosis method comprising:

reconstructing an ultrasonic image captured in real time, on a basis of a reflection echo signal measured by an ultrasonic probe which transmits ultrasonic waves to a subject and receives the ultrasonic waves from the subject;

holding volume data of the subject captured in advance extracting, from the volume data, a reference image corresponding to a sectional position of the ultrasonic image captured in real time; and displaying a reconstructed said ultrasonic image captured in real time and the reference image, wherein:

the holding holds time-series volume data of plural shifted slice-planes of the subject captured in advance, in which time phase information are attributed to two-dimensional image data of respective time-series cross-sectional images taken in each slice-plane; and the extracting acquires, the two-dimensional image data of a time-series cross-sectional image having a slice plane which coincides with a slice plane of the ultrasonic image captured in real time and having time-phase information which coincides with the time-phase information of the ultrasonic image captured in real time, and reconstructs the reference image of the position corresponding to a slice plane of the ultrasonic image captured in real time, from the acquired two-dimensional image data; and when a reference-image display function is started, the ultrasonic diagnosis apparatus checks whether or not the type of a biological signal fed to an input of the ultrasonic diagnosis apparatus in connection with real-time said reflection echo signal measured by an ultrasonic probe, coincides with the type of the biological signal added to the two-dimensional image data of respective cross-sections of the volume data, and provides a warning when coincidence is not found.

* * * * *